United States Patent [19]

Brandfield

[11] Patent Number: 4,669,470
[45] Date of Patent: Jun. 2, 1987

[54] SURGICAL FORCEPS/SCISSORS

[76] Inventor: Robert T. Brandfield, 30 Beechwood, Oakland, Calif. 94618

[21] Appl. No.: 799,812

[22] Filed: Nov. 20, 1985

[51] Int. Cl.$^4$ .............................................. A61B 17/32
[52] U.S. Cl. .................................................... 128/318
[58] Field of Search ...................... 128/318, 305, 354; 30/179-188, 124

[56] References Cited

U.S. PATENT DOCUMENTS 4,034,473  7/1977  May ..................................... 128/318
4,053,979 10/1977  Tuthill et al. ........................ 128/318

FOREIGN PATENT DOCUMENTS 1183358  4/1902  France ................................. 128/318
2371912  7/1978  France ................................. 128/318

*Primary Examiner*—John D. Yasko
*Attorney, Agent, or Firm*—Townsend and Townsend

[57] ABSTRACT

An improved combination forceps and cutting instrument. A pair of opposed elongated metal arms are coupled to a first end and have opposing planar forceps-grasping surfaces at a second end. Behind this second end are a pair of opposed cutting blades extending inward from the arms. The cutting blades are perpendicular to the arms and form a scissors type cutting mechanism. The blades are biased towards each other so that the cutting edges scrape each other as the instrument is closed.

9 Claims, 5 Drawing Figures

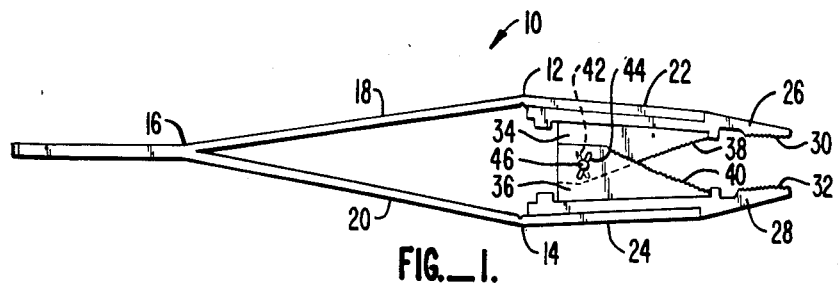
FIG._1.
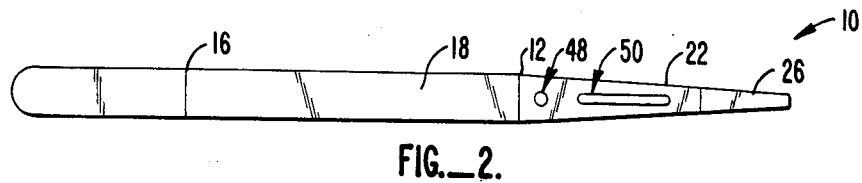
FIG._2.
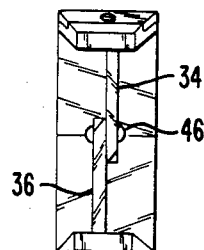
FIG._3.
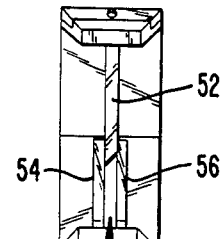
FIG._5.
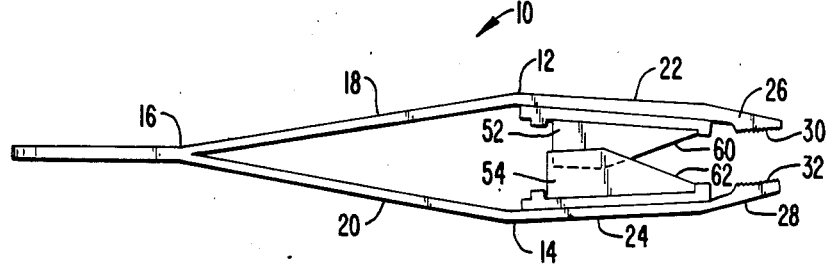
FIG._4.

SURGICAL FORCEPS/SCISSORS

BACKGROUND OF THE INVENTION

The present invention relates to surgical instruments and in particular to combined forceps and scissors for suturing.

Presently, when suturing, doctors will use a forceps to grasp a wound, pull a suture through a wound, then put the forceps down and pick up a scissors to cut the suture. This is a somewhat awkward operation and requires the presence of many tools, each of which must be sterilized. It would be desirable to have one tool which the doctor could use to both grasp a wound while pulling the suture or needle through the wound and subsequently cut the suture.

A tool for holding a suture while it is being cut is shown in U.S. Pat. No. 3,443,313 to Profy. Profy shows a scissors with a hemostat grasping surface at the end which closes before the scissors blade closes. Thus, a doctor can use the Profy device to grasp a suture and then apply more pressure to the scissors handles to then cut the suture. A forceps is still required to grasp the wound because hemostats are not designed to grasp skin. If a doctor tried to use the Profy device simply for grasping a suture or anything else without cutting it, the doctor may apply too much pressure and inadvertently cut the suture at an inappropriate position.

SUMMARY OF THE INVENTION

The present invention is an improved combination forceps and cutting instrument. A pair of opposed elongated metal arms are coupled at a first end and have opposing planar forceps-grasping surfaces at a second end. Behind this second end are a pair of opposed cutting blades extending inward from the arms. The cutting blades are perpendicular to the arms and form a scissors type cutting mechanism. The blades are biased towards each other so that the cutting edges scrape each other as the instrument is closed.

The unique arrangement of the present invention allows the instrument to be used as a forceps with a wound being grasped at its tip between the planar surfaces. When the instrument is desired to be used as a scissors, the suture is placed past the tips of the instrument between the cutting blades and the suture is severed upon closing the instrument.

In one embodiment, each of the cutting blades has an elongated slot substantially perpendicular to the arms of the instrument. A rivet passes through the slot to hold the blades together. The slot is shaped so that when the blades close the rivet does not bind the blades but freely passes through the slot while keeping the blades scraping each other. Thus, the slot has a slight arc to it to complement the arc in which the arms move when they close. In addition, the cutting blades have edges which extend away from the tips of the instrument at an angle to the arms so that they form jaws which close when the instrument is closed. Preferably, at least one of the blades has a serrated edge to aid in cutting.

In an alternate embodiment, no slots and rivet are present, but instead a second blade-like member extends from one of the arms parallel to the blade on that arm. This parallel member thus forms a slot between it and the other blade into which the blade on the opposing arm extends in a guillotine-like arrangement. Thus, this additional blade-like member forces the blades against each other to provide the necessary scraping motion for cutting.

For a further understanding of the nature and advantages of the invention, reference should be made to the ensuing detailed description taken in conjunction with the accompanying drawings.

BRIEF DESCRIPTION OF THE DRAWINGS

FIG. 1 is a side elevation view of a preferred embodiment of a combination forceps and scissors according to the present invention;

FIG. 2 is a top elevation view of the embodiment of FIG. 1;

FIG. 3 is a front elevation view of the embodiment of FIG. 1;

FIG. 4 is an alternate embodiment of a combination forceps and scissors according to the present invention; and FIG. 5 is a front elevation view of the embodiment of FIG. 4.

DETAILED DESCRIPTION OF THE PREFERRED EMBODIMENTS

FIG. 1 shows a combination forceps/scissors 10 according to the present invention. A pair of arms 12, 14 are coupled together at a joint 16. Arms 12 and 14 diverge outwardly for a first portion 18, 20, respectively. Arms 12, 14 diverge inwardly from first portions 18, 20 for second portions 22, 24. A pair of forceps tips 26, 28 are attached to portions 22, 24 and have opposing surfaces 30, 32, respectively, with small teeth for atraumatically grasping tissue.

A pair of cutting blades 34, 36 extend inward from portions 22 and 24 of arms 12, 14. Blades 34, 36 have cutting edges 38, 40, respectively. Blades 34, 36 have slots 42, 44, respectively, through which passes a rivet 46. Slots 42, 44 are substantially perpendicular to portions 22, 24 of arms 12, 14 with a slight arc so that rivet 46 will hold blades 34, 36 together but not cause binding when the arms are closed. Preferably, at least one of edges 38, 40 of cutting blades 34, 36 are serrated.

Blades 34 and 36 can be attached to members 26 and 28 which can be manufactured separate from arms 12 and 14. Members 26 and 28 can be attached to arms 12 and 14 as shown in FIG. 2 by press fit through a hole and slot 48, 50, respectively. Blades 34, 36 are attached to members 26, 28 so that different blade shapes could be added to arms 12, 14. In addition, arms used for ordinary forceps could be easily used to form the instrument of the present invention.

FIG. 3 shows a side view of the combination forceps/scissors 10 of FIG. 1. As can be seen, rivet 46 holds blades 34, 36 together so that edges 38, 40 will scrape against each other to provide a cutting action.

An alternate embodiment of the forceps/scissors is shown in FIG. 4. The instrument of FIG. 4 is identical to that of FIG. 1 except that a pair of cutting blades 52, 54 do not have any slots in them. As can best be seen from the front elevation view of FIG. 5, a second blade-like member 56 is arranged in parallel to blade 54 with blade 52 extending into a slot 58 formed between blade 54 and member 56. Member 56 thus forces blade 52 up against blade 54 to provide the proper scraping action for cutting. Blade 52 will extend into slot 58 even when arms 12, 14 are open so that the blades do not become misaligned. Again, blades 52 and 54 have cutting edges 60, 62, respectively. Preferably, at least one of edges 60, 62 is serrated to improve the cutting action of the instrument.

As will be understood by those familiar with the art, the present invention can be embodied in other specific forms without departing from the spirit or essential characteristics thereof. For example, a scissors type two-armed handle could be used rather than the single piece joint 16 shown in FIG. 1. Accordingly, the foregoing embodiments are intended to be illustrative of, but not limiting of, the scope of the invention which is set forth in the following claims.

What is claimed is:

1. A forceps and cutting instrument comprising:
   a pair of opposed, elongated metal arms immovably coupled at a first end and having opposing planar surfaces at a second end for grasping objects therebetween;
   a pair of opposed cutting blades extending inward from said arms, said blades being rearward of said second end of said arms, each blade having a planar surface perpendicular to one of said arms, said blades being offset so that said blades extend past each other when said arms are closed toward each other; and
   means for biasing said planar surfaces of said blades toward each other when said arms are closed.

2. A forceps and cutting instrument comprising:
   a pair of opposed, elongated metal arms coupled at a first end and having opposing planar surfaces at a second end for grasping objects therebetween;
   a pair of opposed cutting blades extending inward from said arms, said blades being rearward of said second end of said arms, each blade having a planar surface perpendicular to one of said arms, said blades being offset so that said blades extend past each other when said arms are closed toward each other, said blades having aligned slots; and
   means for biasing said planar surfaces of said blades toward each other when said arms are closed, said biasing means comprising a member extending through said slots, said member having ends which are wider than said slots.

3. The instrument of claim 1 wherein said arms are immovably coupled at said first end, each of said arms diverging outwardly for a first portion and extending inwardly from said first portion to said second end, each of said blades being coupled to one of said arms at said second portion.

4. The instrument of claim 3 wherein each of said blades has an inclined, sharp cutting edge extending rearwardly from proximate said second end of said arm and toward the other arm.

5. The instrument of claim 4 wherein said blades have aligned slots and said biasing means comprises a member extending through said slots, said member having ends which are wider than said slots, each slot being elongated in a direction substantially perpendicular to said second portion of one of said arms and said slots being curved so that said member moves freely through said slots without binding when said arms are closed towards each other.

6. The instrument of claim 3 wherein said biasing means comprises a planar member parallel to one of said blades and defining a slot between said planar member and said one of said blades for receiving the other one of said blades.

7. The instrument of claim 3 wherein at least one of said blades has a serrated cutting edge.

8. The instrument of claim 3 wherein said opposing planar surfaces at said second ends of said arms and said blades are removably attached to said arms.

9. A forceps and cutting instrument comprising:
   a pair of opposed, elongated metal arms immovably coupled at a first end, said arms diverging outwardly for a first portion and extending inwardly at a second portion from said first portion to a second end of said arms;
   a pair of opposing planar surfaces coupled to said second ends of said arms for grasping objects therebetween;
   a pair of opposed cutting blades attached to said second portions of said arms, each blade being offset relative to the other so that said blades extend past each other when said arms are closed, said blades having aligned, elongated slots extending in a direction substantially perpendicular to said second portion of said arm, at least one of said blades having a serrated edge extending rearwardly from proximate said second end of said arm and toward the other arm; and
   a rivet extending through said slots for holding said blades in close proximity.

* * * * *